United States Patent
Suehira et al.

(10) Patent No.: US 8,504,141 B2
(45) Date of Patent: Aug. 6, 2013

(54) OPTICAL TOMOGRAPHIC IMAGE GENERATING APPARATUS AND OPTICAL TOMOGRAPHIC IMAGE GENERATING METHOD

(75) Inventors: Nobuhito Suehira, Kawasaki (JP); Mitsuro Sugita, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 301 days.

(21) Appl. No.: 12/893,439

(22) Filed: Sep. 29, 2010

(65) Prior Publication Data
US 2011/0098560 A1   Apr. 28, 2011

(30) Foreign Application Priority Data
Oct. 23, 2009   (JP) .................. 2009-244678

(51) Int. Cl.
*A61B 5/00*   (2006.01)
(52) U.S. Cl.
USPC ........................................ 600/476
(58) Field of Classification Search
USPC ........................................ 600/476
See application file for complete search history.

(56) References Cited

U.S. PATENT DOCUMENTS

| 8,000,774 B2 * | 8/2011 | Sum et al. .................. 600/473 |
| 2008/0175465 A1 | 7/2008 | Jiang et al. |
| 2008/0234972 A1 | 9/2008 | Tsukada et al. |
| 2008/0273783 A1 | 11/2008 | Toth et al. |
| 2010/0166293 A1 | 7/2010 | Sugita et al. |
| 2010/0181462 A1 | 7/2010 | Sugita |
| 2010/0226553 A1 | 9/2010 | Suehira |
| 2010/0226554 A1 | 9/2010 | Suehira |

FOREIGN PATENT DOCUMENTS

| JP | 2008-237238 A | 10/2008 |
| WO | 03/011764 A2 | 2/2003 |

OTHER PUBLICATIONS

Search Report for corresponding European Appln. No. 10188406.2 dated Feb. 17, 2011.

* cited by examiner

*Primary Examiner* — Jonathan Cwern
(74) *Attorney, Agent, or Firm* — Fitzpatrick, Cella, Harper & Scinto

(57) ABSTRACT

The present invention relates to an optical tomographic image generating method including: obtaining signals for a plurality of frames; obtaining respective complex number data by performing Fourier transformation of the signals for the plurality of frames; synthesizing the plurality of frames using the respective complex number data; generating a tomographic image based on the synthesized data. This configuration enables easy enhancement of the image quality in an optical coherence tomographic imaging apparatus.

40 Claims, 5 Drawing Sheets

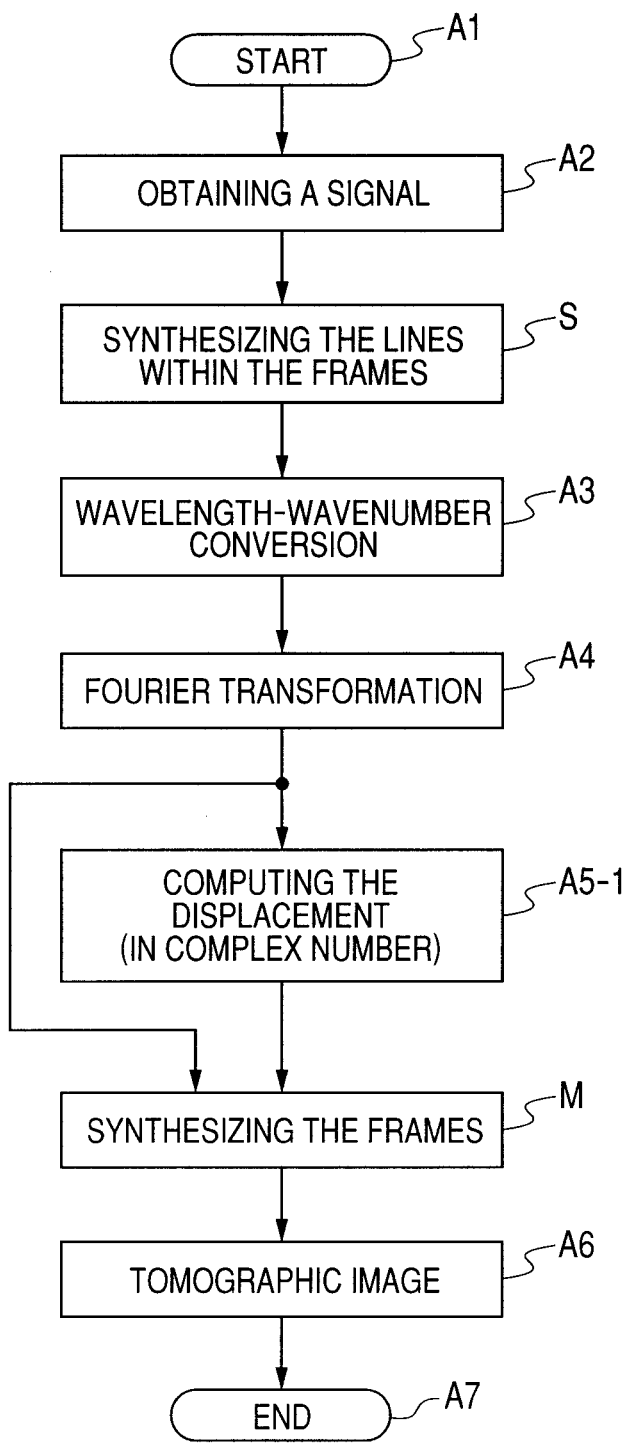

OPTICAL TOMOGRAPHIC IMAGE GENERATING APPARATUS AND OPTICAL TOMOGRAPHIC IMAGE GENERATING METHOD

BACKGROUND OF THE INVENTION

1. Field of the Invention

The present invention relates to an optical tomographic image generating apparatus and an optical tomographic image generating method.

2. Description of the Related Art

Currently, practical imaging apparatuses using optical coherence tomography (OCT) utilize interference of low-coherence light are in use. These apparatuses (hereinafter also referred to as an OCT apparatus) can obtain tomographic images with a depth resolution of several micrometers, enabling provision of high-resolution tomographic images of objects.

Japanese Patent Application Laid-Open No. 2008-237238 discloses an optical image measurement apparatus for enhancing the image quality of the formed images. This apparatus forms a plurality of tomographic images of the fundus of an eye, and stores the formed images. Then, the optical image measurement apparatus performs an arithmetic operation using one of the tomographic images and the tomographic images adjacent thereto, thus enabling the formation of another tomographic image. Consequently, the image quality of formed images can be enhanced.

SUMMARY OF THE INVENTION

However, even though a plurality of tomographic images is formed and arithmetic operation is performed using the pixel values of the tomographic images to form a final tomographic image as in Japanese Patent Application Laid-Open No. 2008-237238, the image quality enhancement may be limited because the noise components are not efficiently removed.

The present invention has been made to solve the above problem, and an object of the present invention is to further enhance the image quality of tomographic images by efficiently removing noise components.

The present inventors have discovered that when an arithmetic operation is performed using a plurality of tomographic images as in Japanese Patent Application Laid-Open No. 2008-237238, efficient noise-reduction is not performed because the arithmetic operation is conventionally performed after conversion of the pixel values of the tomographic images into real numbers. Therefore, the present inventors verified that more efficient noise-reduction can be provided by performing the arithmetic operation with the pixel values kept in complex number form and then converting the complex numbers into real numbers after the arithmetic operation, thereby completing the present invention.

In other words, an optical tomographic image generating method according to the present invention is an optical tomographic image generating method for generating a tomographic image of an object, the method including: obtaining signals for a plurality of frames obtained by applying a light beam to the object; obtaining respective complex number data by performing Fourier transformation of the signals for the plurality of frames; synthesizing the plurality of frames in complex number form using the respective complex number data; and generating a tomographic image based on the synthesized data.

Also, an optical tomographic image generating apparatus according to the present invention is an optical tomographic image generating apparatus in which a light beam from a light source is divided into a measuring beam and a reference beam, the measuring beam is guided to an object via a measuring beam path, and the reference beam is guided to a reference mirror via a reference beam path, and a tomographic image of the object is generated using a combined beam of a return beam that is the measuring beam reflected or scattered by the object, and the reference beam reflected by the reference mirror, the optical tomographic image generating apparatus including: a detecting unit that detects the combined beam; a memory that stores signals for a plurality of frames detected by the detecting unit; a unit that obtains respective complex number data by performing Fourier transformation of the signals for the plurality of frames; a synthesizing unit that performs synthesizing of the plurality of frames in complex number form using the respective complex number data; and a generating unit that generates a tomographic image based on the synthesized data.

According to the present invention, further image quality enhancement can be expected by efficiently removing noise components.

Further features of the present invention will become apparent from the following description of embodiments with reference to the attached drawings.

BRIEF DESCRIPTION OF THE DRAWINGS

FIG. 5 is a diagram illustrating signal processing in Example 2 of the present invention.

DESCRIPTION OF THE EMBODIMENTS

Preferred embodiments of the present invention will now be described in detail in accordance with the accompanying drawings.

Figure 1:
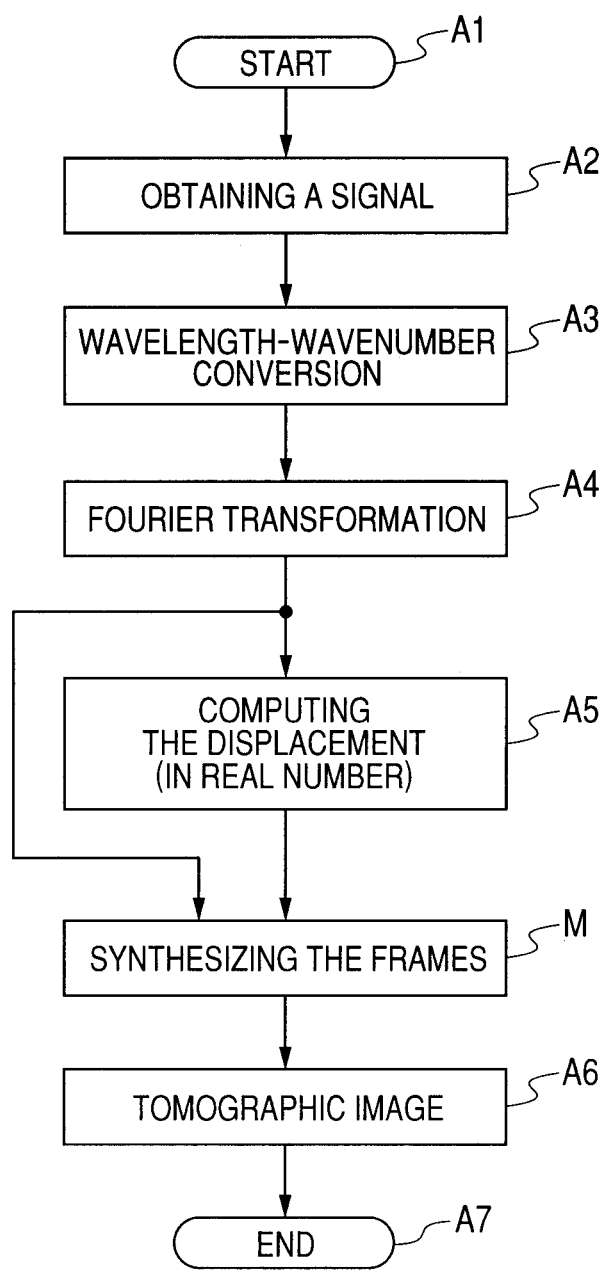
FIG. 1 is a diagram illustrating signal processing in Example 1 of the present invention.

An embodiment of the present invention provides an optical tomographic image generating method for generating a tomographic image of an object, the method including: obtaining signals for a plurality of frames obtained by applying a light beam to the object; obtaining respective complex number data by performing Fourier transformation of the signals for the plurality of frames; synthesizing the plurality of frames in complex number form using the respective complex number data; generating a tomographic image based on the synthesized data. As illustrated in FIGS. 1 and 5, the displacement of the frames may be computed before synthesizing the signals, to synthesize the plurality of frames based on such information.

Example 1

Next, Example 1 of the present invention will be described. Although in the present example a tomographic image is generated by an imaging apparatus using a Michelson interferometer, an imaging apparatus that can be used for the present invention is not limited to this apparatus, and any type of interferometer, such as a Mach-Zehnder interferometer, for example, can be employed. Also, in the signal processing in the present example, a displacement computation is performed based on real number data, which is different from Example 2 described later.

(Michelson Interferometer)

Figure 2:
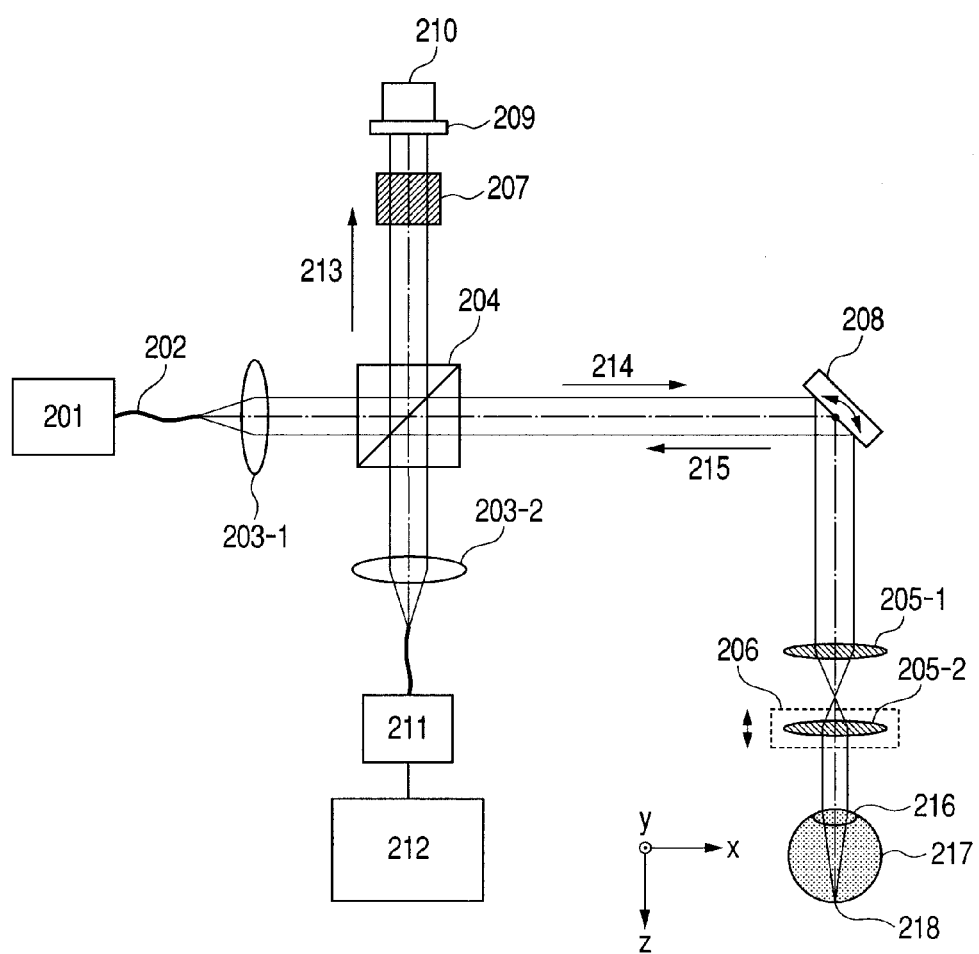
FIG. 2 is a diagram illustrating a Michelson-type OCT apparatus in Example 1 of the present invention.

An optical coherence tomographic imaging apparatus according to Example 1 will be described with reference to FIG. 2. FIG. 2 is a schematic diagram illustrating an imaging apparatus using a Michelson-type optical system (Michelson interferometer) according to the present example.

A light beam emitted from a light source 201, which is transmitted through a fiber 202 and a lens 203-1, is divided by a beam splitter 204 into a measuring beam 214 and a reference beam 213. The measuring beam 214 enters an eye 217, which is an object, via an XY scanner 208 and objective lenses 205-1 and 205-2. Then, the measuring beam 214 that has entered the eye passes through a cornea 216 and then reaches a retina 218.

The return beam 215 reflected and scattered by the retina 218 of the eye 217 returns to the objective lens 205-2 and 205-1, the XY scanner 208 and the beam splitter 204 in this order. Furthermore, the return beam 215 is guided to a spectroscope 211 via a lens 203-2. The spectroscope 211 includes, e.g., a lens, a grating and an image sensor. For the image sensor, a CCD or CMOS line sensor may be used. Signals obtained by the line sensor in the spectroscope 211 are sent to a computer 212 and stored in a memory, and the later-described processing is performed on the signals.

Meanwhile, the reference beam 213 is reflected by a reference mirror 209 via a dispersion compensation glass 207, and passes through the dispersion compensation glass 207 again and returns to the beam splitter 204. The dispersion compensation glass 207 is provided for compensating for dispersion caused by the eye 217 and the objective lenses 205-1 and 205-2. The reference mirror 209 can adjust the length of the optical path of the reference beam by means of a mirror adjustment mechanism 210. The reference beam 213 and the return beam 215 are combined by the beam splitter 204. Then, this combined beam is guided to the spectroscope 211 and detected by the spectroscope 211. In the measuring beam path, a portion with its length coincident with that of the reference beam is referred to as a coherence gate. When measuring the retina 218 of the eye 217, the position of the reference mirror 209 is adjusted so that the coherence gate is close to the retina 218.

For the light source 201, a superluminescent diode (SLD), which is a typical low-coherence light source, may be used. A light beam from the light source 201 has, for example, a central wavelength of 840 nm and a bandwidth of 50 nm. It should be noted that a band width is an important parameter because it affects the resolution in the optical axis direction of an obtained tomographic image. Also, although the type of the light source 201 is an SLD, here, any light source that can emit low-coherence light may be employed, and, e.g., amplified spontaneous emission (ASE) may be used. It should be understood that depending on the nature of the object, another light source such as a halogen lump may be used. However, since the wavelength affects the resolution in the traverse direction of an obtained tomographic image, the wavelength is desirably short where emphasizing the resolution in the traverse direction.

The computer 212 controls the spectroscope 211, the XY scanner 208, the mirror adjustment mechanism 210, and a focusing mechanism 206, in addition to computing and controlling described later. It should be understood that the computer 212 can also perform, e.g., data input, image processing, image display and data storage.

(Signal Processing Process)

Signal processing performed by the OCT apparatus illustrated in FIG. 2 will be described using FIG. 1.

Measurement is started in step A1. In this state, the OCT apparatus is activated and an eye of interest is set in place. Furthermore, necessary adjustments have been made by an operator and measurement has been started.

Figures 3A, 3B, 3C:
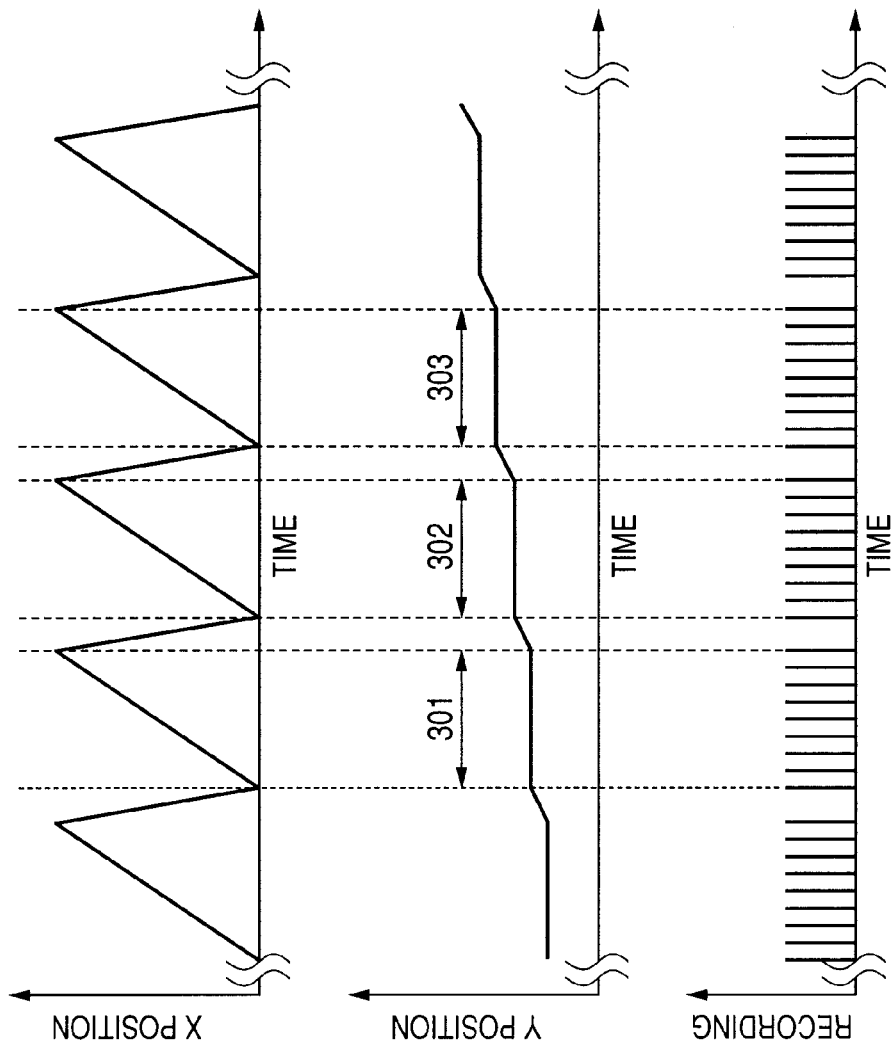
FIGS. 3A, 3B and 3C are diagrams illustrating a time chart in Example 1 of the present invention.

In step A2, signals are obtained. Here, the case where a three-dimensional image is obtained by two-dimensionally scanning the retina 218 by means of the XY scanner 208 while applying the measuring beam 214 to the retina 218 of a fundus will be described. In FIG. 2, an X direction perpendicular to the optical axis of an eye is a fast scan direction, and a Y direction is a slow scan direction. FIGS. 3A, 3B and 3C are timing charts illustrating X position, Y position and recording timing, respectively. When recording is performed 512 consecutive times in the X direction with the Y position fixed, data for one frame, which includes 1024×512 elements, is obtained if the number of pixels in the line sensor in the spectroscope 211 is 1024. A tomographic image along the X-Z plane can be obtained from the data for one frame, which has been obtained as described above. Furthermore, while moving the XY scanner 208 in the Y direction for 500 steps, the consecutive recording in the X direction is performed for each of the steps, resulting in obtainment of data for 500 frames. FIGS. 3A, 3B and 3C illustrate obtainment of three frames to be synthesized, a first frame 301, a second frame 302 and a third frame 303, from among the 500 frames. The time between the frame recordings is used for, e.g., displacement of the scanner in the X and Y directions for recording in the next position, and data transfer to the computer 212.

It should be understood that the scan pattern is not limited thereto, and images of a plurality of frames having the same Y position may be taken to subsequently synthesize the images. Also, data may be obtained not only by movement of the scanner in a linear direction such as the X direction or the Y direction, but also by rotating the scanner like circle scanning.

In the present example, data for frames having different Y positions in the respective steps of the Y direction is obtained. Here, if the difference in position between the obtained frames is large, the signal components may be corrupted when synthesizing the data (data to be synthesized may cancel each other out, resulting in loss of the original signal components). Therefore, the positional difference in the Y direction is desirably no more than several times the traverse resolution of the OCT apparatus (which is generally determined by the beam diameter of the measuring beam on the object to be measured). In the case of the present example, where the beam diameter of the measuring beam on the object to be measured is around 5 micrometers, the positional difference is around a few tens of micrometers in the Y direction.

In step A3, wavelength-wavenumber conversion is performed. In general, data from the spectroscope 211 includes wavelengths and the intensities in the wavelengths. The wavelengths are usually sampled at regular intervals. First, a function of the intensity data relative to the wavelengths is created. Next, the respective wavelengths are converted into wavenumbers to create a function of the intensity data relative to the wavenumbers. Since a wavenumber is the reciprocal of a wavelength, the wavenumbers do not have regular intervals if they are used as they are. So, wavenumbers are newly allocated so that the 1024 wavenumbers have regular intervals. Then, intensity data corresponding to these wavenumbers is computed. The computation method may be, for example, interpolation such as general linear interpolation or spline interpolation. The computation is desirably a linear operation. Consequently, a two-dimensional array of 1024×

512 elements, which include wavenumbers with regular intervals and the intensities for the wavenumbers, is obtained for each frame. It should be understood that where the spectroscope 211 can perform sampling of the wavenumbers at regular intervals, or where an error due to the wavelength-wavenumber conversion causes no problem, step A3 can be skipped.

In step A4, a Fourier transformation is performed. Here, the discrete Fourier transformation of intensity data having regular intervals relative to the wavenumbers is performed for the respective columns. Consequently, a two-dimensional array of 1024×512 complex numbers is obtained for each frame. However, because of the nature of Fourier transform, the m-th row and the (1024-m)-th row in each column have the same intensity. Accordingly, the 0th to 511th rows are extracted to obtain a two-dimensional array of 512×512 complex numbers, and such data are sent to the following step.

In step A5, the displacement between frames of which signals are to be synthesized is computed. Here, computation of the displacement of the image of the second frame 302 and the image of the third frame 303 relative to the image of the first frame 301 will be described. First, 512×512 complex number data for each frame is converted into real numbers.

Here, an i column (512 elements) in the image of the second frame 302 is selected relative to the 128th column (384 elements in 65th to 448th rows) of the first frame 301, and the difference between the 384 elements of the first frame 301 and the consecutive 384 elements from a j row in the i column is computed to obtain a one-dimensional array. The mean square of the elements in the one-dimensional array and the elements selected in the first frame is obtained. This calculation is performed for necessary i columns and j rows, and from among the i columns and j rows, $i_1$ and $j_1$ having the smallest mean square are determined. Next, similar calculation is performed for the 384th column (384 elements in the 65th to 448th rows) of the first frame 301 to determine $i_2$ and $j_2$ having the smallest mean square. Consequently, the displacement of the image of the second frame 302 relative to the image of the first frame 301 is obtained. If the displacement is zero, $i_1=128$, $j_1=65$, and $i_2=384$, $j_2=65$.

Furthermore, the displacement of the image of the third frame 303 is obtained relative to the image of the first frame 301 in a similar manner. Then, the information on the computed displacements is sent to step M.

The above method may be repeated to enhance the accuracy of the information on the displacements, or the displacements of subpixels may be computed by performing interpolation for each column. It should be understood that another method may be employed for the displacement computation.

In step M, the signals are synthesized. The two-dimensional complex number data obtained in step A4 are averaged based on the information on the displacements obtained in step A5. The complex number data for the second frame 302, which is a result of parallel or rotational displacement, is added to the complex number data for the first frame 301. It should be understood that since the array is a discrete one, necessary interpolation processing has been applied to the image of the second frame 302. The complex number data for the third frame 303, which is also a result of parallel or rotational displacement, is further added to the complex number data 301 with the complex number data for the second frame 302 added thereto. Then, the synthesized complex number data is converted into real numbers and sent to step A6.

Although weighted averaging may be employed for the averaging, the effect of noise-reduction may vary if different weights are provided to the complex numbers. It should be noted that frame data determined to have a measurement error may be taken out.

In step A6, the data is shown in a display screen of the computer 212 as one tomographic image.

Then, the processing ends in step A7.

Although the processing from measurement using an OCT apparatus to image display has been described here, for example, an image with its noise reduced may be obtained by applying the above-described processing to data for a plurality of frames obtained via a network.

In the present example, when synthesizing data for a plurality of frames, displacement computation is performed based on the real number data, synthesizing is performed based on the complex number data, enabling provision of effective reduction of noise, and thus, further image quality enhancement can be expected.

(Description of the Principle)

In step M in the present example, frame images are added up in complex number form and subsequently the complex numbers are converted into real numbers, while in conventional techniques, after conversion into real numbers, frame images are added up to synthesize the signals. The difference in principle between these methods boils down to the difference between the case where two complex numbers are added up after they are converted into real numbers, and the case where two complex numbers are added up before conversion into real numbers, and subsequently converted into real numbers.

Here, using imaginary unit i, elements 1 and 2 in complex number are expressed by Expressions 1-1 and 1-2, respectively.

$$a_0+b_0 i = r_0 e(i\phi_0) \qquad \text{(Expression 1-1)}$$

$$a_1+b_1 i = r_1 e(i\phi_1) \qquad \text{(Expression 1-2)}$$

The result of adding up elements 1 and 2 in complex number form and then converting the elements into real numbers is expressed by Expression 2.

$$\sqrt{(a_0+a_1)^2+(b_0+b_1)^2} \qquad \text{(Expression 2)}$$

The result of adding up elements 1 and 2 after converting the elements into real numbers is expressed by Expression 3.

$$\sqrt{a_0^2+b_0^2}+\sqrt{a_1^2+b_1^2} \qquad \text{(Expression 3)}$$

Expressions 2 and 3 have the relationship expressed by Expression 4 when Expressions 2 and 3 are raised to the second power and the common term is deducted from Expressions 2 and 3. (The relationship can easily be proven when both sides are further raised to the second power.)

$$a_0 a_1+b_0 b_1 \leq \sqrt{a_0^2+b_0^2}\sqrt{a_1^2+b_1^2} \qquad \text{(Expression 4)}$$

In other words, the value of Expression 2 is no more than the value of Expression 3. This is important in noise-reduction. That is, in the case of random noise, the noise includes positive components and negative components. If the elements are added up in complex number form, the positive components and the negative components of the noise cancel each other out, and thus, more efficient averaging can be performed. Using linear transformation in the respective steps of the signal processing, the same result can be obtained even if data before conversion into complex numbers are superimposed on another data.

Table 1 indicates comparison of signal/noise ratios (SNR). This result is somewhat different from the result obtained by the process in the present example because as in Example 2, which will be described later, the lines in frames are synthesized. However, the table provides data sufficient for comparison of SNRs in terms of the timing of conversion of pixel values into real numbers. For the recording object, the range of around 6 mm of the retina of a normal eye with the macula as its center was measured. The number of lines is 2048. Using the same original data, (1) the 2048 lines were reduced to 512 lines by extracting a line every four lines from the 2048 lines to generate a tomographic image for one frame, which has not been objected to synthesizing, (2) the 2048 lines were reduced to 1024 lines by extracting a line every two lines, and adjacent two lines are synthesized to generate a tomographic image for one frame, which has 512 lines, and (3) consecutive four lines in the 2048 lines were synthesized to generate a tomographic image for one frame, which has 512 lines. For the respective cases, the table indicates comparison between the SNR where synthesizing was performed before conversion from complex numbers to real numbers, and the SNR after conversion into real numbers. The case where synthesizing was performed before conversion into real numbers (corresponding to frame synthesizing in complex number form in the present example) shows that as the number of lines to be synthesized is larger, the SNR is improved more. Meanwhile, the case where synthesizing was performed after conversion into real numbers shows that the SNRs are roughly constant. However, regardless of when to perform conversion into real numbers, comparing the case where synthesizing (averaging) was not performed and the case where synthesizing was performed after conversion into real numbers, the case where synthesizing was performed provides a smoother image. Here, a SNR is the ratio of the smallest value among the root mean square (RMS) of noise in each line to the largest value among the pixels.

TABLE 1

Comparison of SNRs [dB]

| | Synthesizing before conversion into real numbers | Synthesizing after conversion into real numbers |
|---|---|---|
| 512 (No averaging performed) | 40.22 | 40.22 |
| 1024 (Two lines averaged) | 42.84 | 40.27 |
| 2048 (Four lines averaged) | 45.74 | 40.35 |

Example 2

Next, Example 2 of the present invention will be described. Here, the description will be given especially for differences from Example 1. In the present example, a tomographic image is generated by means of an imaging apparatus using a Mach-Zehnder interferometer. However, an imaging apparatus that can be used in the present invention is not limited to this interferometer, and for example, any interferometer, such as a Michelson interferometer, can be employed. Also, signal processing in the present example includes synthesizing signals of a frame in the frame, and computing a displacement including phase components. Although a mode including both of these features will be described below, the present invention is not limited to the below description, and the present invention may be applied to a mode including only one of the features.

(Mach-Zehnder Interferometer)

Figure 4:
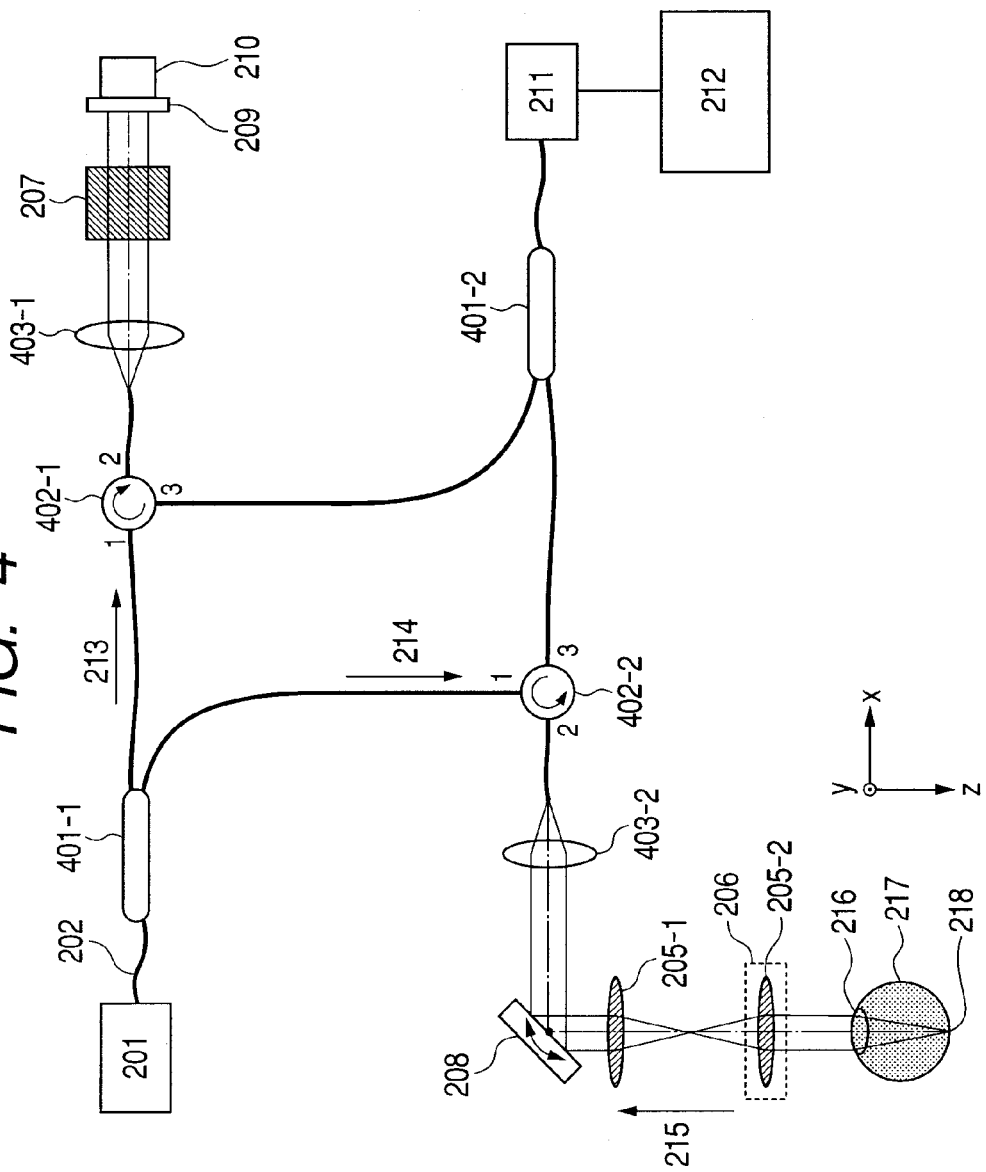
FIG. 4 is a diagram illustrating a Mach-Zehnder-type OCT apparatus in Example 2 of the present invention.

An imaging apparatus using an optical coherence tomographic method according to Example 2 will be described using FIG. 4. FIG. 4 is a schematic diagram illustrating an imaging apparatus using a Mach-Zehnder-type optical system in the present example. The same components as those in FIG. 2 are provided with the same symbols, and a part of the description will be omitted. A light beam emitted from a light source 201 is transmitted via a fiber 202 and divided into a measuring beam 214 and a reference beam 213 by a fiber coupler 401-1.

The measuring beam 214 enters a port 1 of a circulator 402-2 and exits from a port 2 of the circulator 402-2, and reaches a lens 403-2. Furthermore, the measuring beam 214 reaches a retina 218 via an XY scanner 208, objective lenses 205-1 and 205-2, and a cornea 216. A return beam 215 scattered and reflected by the retina 218 returns to the objective lenses 205-2 and 205-1 and the XY scanner 208, enters the port 2 of the circulator 402-2 and exits from a port 3 of the circulator 402-2, and reaches a fiber coupler 401-2.

Meanwhile, the reference beam 213 enters a port 1 of a circulator 402-1 and exits from a port 2 of the circulator 402-1, and is transmitted via a lens 403-1 and a dispersion compensation glass 207 and reflected by a reference mirror 209. The reflected reference beam 213 returns to the lens 403-1 and the port 2 of the circulator 402-1 via the dispersion compensation glass 207, and exits from the port 3 of the circulator 402-1, and reaches the fiber coupler 401-2. The reference mirror 209 can adjust the optical path length by means of a mirror adjustment mechanism 210. The reference beam 213 and the return beam 215 are combined by the fiber coupler 401-2, and the combined beam is guided to a spectroscope 211 and detected, and sent to a computer 212.

(Signal Processing Process)

Using FIG. 5, signal processing in Example 2, which is performed by the OCT apparatus illustrated in FIG. 4, will be described. The same symbols as those in FIG. 1 represent similar processing.

Measurement starts in step A1.

Signals are obtained in step A2. Here, an image with 2048 lines is obtained for one frame, and 500 such frames are obtained. Consequently, data of 1024×2048 elements is obtained per frame. Here, one of the features of the present example is that signals are synthesized in the respective frames.

Regardless of whether signals are synthesized in the frames or between the frames, the effect of noise-reduction is the same in principle if an object does not move. However, the problem is not simple where the object is a moving one like an eye. Where the line rate is 20 kHz, the time required for obtaining data for one frame is 26 msec for 512 lines, and 102 msec for 2048 lines. Adding 4 msec, which is the time required for the scanner to return, to that time, the frame intervals are around 30 msec and 106 msec, respectively. In other words, although displacement computation is not required for synthesizing adjacent lines in a frame, however, where the time of measuring a frame becomes longer, the probability of strain or falling-out of data caused by closing an eye in the frame occurring will increase. Also in the present example, for the same reason as in Example 1, the difference in position between the obtained lines is desirably not more than several times the beam diameter.

In step S, adjacent lines in each frame are synthesized. Every four adjacent lines in 2048 lines are synthesized to obtain data having 1024×512 elements for each frame.

In step A3, wavelength-to-wavenumber conversion is performed.

In step A4, Fourier transform is performed. Then, necessary parts are clipped to obtain a two-dimensional-array data of 512×512 complex numbers for each frame, and the data is sent to the next step.

In step A5-1, the displacement is computed. Here, while in Example 1, the displacement computation has been performed after conversion into real numbers, in the present example, the displacement computation is performed in complex number form. In other words, the difference between the data is computed in complex number form, and the displacement for the case where the mean square of the computation result is the smallest is extracted. Consequently, the displacement including phases can be computed.

The computation may be performed after converting the complex number data into polar coordinates.

In step M, averaging of the two-dimensional array data of complex numbers obtained in step A4 is performed based on the information relating to the displacement including phases obtained in step A5-1. Then, the result is converted into real numbers and such data is sent to step A6.

In step A6, one tomographic image is obtained.

In step A7, the processing ends.

In the present example, the displacement including phases can be computed, enabling further image quality enhancement to be expected.

Example 3

Also, the present invention can be practiced by performing the following processing. In other words, software (computer program) providing the functions provided by the above-described embodiments is supplied to a system or an apparatus via a network or a recording medium of various types, and a computer (or a CPU or MPU or the like) in the system or the apparatus reads and executes the program.

In other words, the computer program includes obtaining signals for a plurality of frames by applying a light beam to an object; obtaining respective complex number data by performing Fourier transformation of the signals for the plurality of frames; synthesizing the plurality of frames in complex number form using the respective complex number data; and generating a tomographic image based on the synthesized data. Furthermore, the computer program may further include obtaining frame displacement information, and synthesizing signals for a frame within the frame.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium). In such a case, the system or apparatus, and the recording medium where the program is stored, are included as being within the scope of the present invention.

While the present invention has been described with reference to embodiments, it is to be understood that the invention is not limited to the disclosed embodiments.

This application claims the benefit of Japanese Patent Application No. 2009-244678, filed Oct. 23, 2009, which is hereby incorporated by reference herein in its entirety.

What is claimed is:

1. An optical tomographic image generating method that generates a tomographic image of an object, the method comprising:
    obtaining intensity signals for each of a plurality of frames obtained by applying a light beam to the object;
    obtaining respective complex number data by performing discrete Fourier transformation of the intensity signals for each of the plurality of frames;
    obtaining frame displacement information between the frames, based on a result of converting the complex number data into real number data;
    synthesizing the plurality of frames in complex number form by averaging the respective complex number data from each of the plurality of frames based on the frame displacement information; and
    generating the tomographic image based on the synthesized frames in complex number form.

2. The optical tomographic image generating method according to claim 1, wherein said synthesizing step is performed by averaging the plurality of frames with the frames weighted according to the obtained frame displacement information.

3. The optical tomographic image generating method according to claim 1, wherein said synthesizing step is performed by averaging a result of one of parallel and rotational displacement of complex number data corresponding to each of the plurality of frames, based on the frame displacement information.

4. The optical tomographic image generating method according to claim 1, further comprising:
    obtaining each one of the plurality of frames by synthesizing intensity signals acquired within a scanning time necessary for scanning the object in a predetermined direction perpendicular to an optical axis of the object,
    wherein synthesizing intensity signals is performed before synthesizing of the plurality of frames in complex number form.

5. The optical tomographic image generating method according to claim 1, further comprising adjusting positions of the plurality of frames based on the frame displacement information before the synthesizing step,
    wherein in said synthesizing step the plurality of frames are synthesized in complex number form by averaging the respective complex number data of each of the plurality of frames after the adjusting adjusts the positions based on the frame displacement information, which is obtained by using a mean square.

6. The optical tomographic image generating method according to claim 1, further comprising adjusting positions of the plurality of frames before the synthesizing step.

7. The optical tomographic image generating method according to claim 1, wherein in the synthesizing step complex number form data of each of the plurality of frames are averaged after the frames are subjected to one of parallel displacement and rotational displacement based on the frame displacement information.

8. The optical tomographic image generating method according to claim 1, further comprising taking out a frame, wherein in the synthesizing step the respective complex number data from each of a plurality of frames which are not taken out are averaged.

9. The optical tomographic image generating method according to claim 8, further comprising determining whether or not a measurement error has occurred in a frame, wherein in the taking out step a frame which is determined to have the measurement error is taken out.

10. The optical tomographic image generating method according to claim 9, wherein in the determining step strain or falling-out of data caused by closing an eye in the frame is determined as the measurement error.

11. The optical tomographic image generating method according to claim 1, wherein in the synthesizing step the respective complex number data are averaged based on information of one of parallel displacement and rotational displacement.

12. The optical tomographic image generating method according to claim 11, wherein the object is an eye, and
wherein the displacement is a result of an eye movement.

13. The optical tomographic image generating method according to claim 1, wherein in the synthesizing step the respective complex number data are subjected to averaging after the obtaining obtains the frame displacement information using a mean square.

14. The optical tomographic image generating method according to claim 1, wherein the object is an eye,
wherein the plurality of frames are obtained in a direction intersecting an optical axis of the eye, and
wherein a positional difference between the frames is no more than several times of a traverse resolution.

15. The optical tomographic image generating method according to claim 1, further comprising displaying the generated tomographic image.

16. The optical tomographic image generating method according to claim 1, further comprising converting the averaged complex number data into real number data,
wherein in the generating the tomographic image, the tomographic image is generated based on the real number data.

17. An optical tomographic image generating apparatus comprising:
a detecting unit that detects a combined beam of a return beam from an object irradiated with a measuring beam and a reference beam corresponding to the measuring beam;
a complex number obtaining unit that obtains respective complex number data by performing discrete Fourier transformation of intensity signals for a plurality of frames detected by said detecting unit;
a frame displacement information obtaining unit that converts the complex number data into real number data and that obtains frame displacement information between the plurality of frames based on a result of the conversion;
a synthesizing unit that synthesizes the plurality of frames in complex number form by averaging the respective complex number data from each of the plurality of frames, based on the frame displacement information; and
a generating unit that generates a tomographic image based on the synthesized data.

18. The optical tomographic image generating method according to claim 17, wherein said synthesizing unit synthesizes the plurality of frames by averaging the plurality of frames with the frames weighted according to the obtained frame displacement information.

19. The optical tomographic image generating apparatus according to claim 17, further comprising:
an intensity signals synthesizing unit that synthesizes intensity signals for a frame within the frame by synthesizing data for adjacent lines in the frame,
wherein said frame displacement information obtaining unit is arranged to obtain the frame displacement information for which the synthesizing has been performed within the respective frames.

20. The optical tomographic image generating apparatus according to claim 17, further comprising:
an intensity signals synthesizing unit that synthesizes intensity signals for a frame within the frame by synthesizing data for adjacent lines in the frame,
wherein said intensity signals synthesizing unit is arranged to synthesize each of a plurality of frames for which the synthesizing has been performed within the respective frames.

21. The optical tomographic image generating apparatus according to claim 17, wherein said synthesizing unit synthesizes the plurality of frames in complex number form by averaging a result of one of parallel and rotational displacement of complex number data corresponding to each of the plurality of frames, based on the frame displacement information.

22. The optical tomographic image generating apparatus according to claim 17, wherein the synthesizing between the frames is performed using signals having a difference in position of not more than several times a beam diameter of the measuring beam.

23. The optical tomographic image generating apparatus according to claim 17, wherein the averaging is obtaining one of mean square and adding average.

24. A non-transitory computer-readable storage medium that stores a computer program that causes a programmable apparatus, upon execution of the program by the apparatus, to perform the optical tomographic image generating method as claimed in claim 1.

25. An optical tomographic image generating apparatus that generates a tomographic image of an object, the apparatus comprising:
a unit that obtains intensity signals for each of a plurality of frames obtained by applying a light beam to the object;
a unit that obtains respective complex number data by performing discrete Fourier transformation of the intensity signals for each of the plurality of frames;
a unit that obtains frame displacement information between the frames, based on a result of converting the complex number data into real number data;
a unit that synthesizes the plurality of frames in complex number form by averaging the respective complex number data from each of the plurality of frames based on the frame displacement information; and
a unit that generates the tomographic image based on the synthesized frames in complex number form.

26. The optical tomographic image generating apparatus according to claim 25, wherein the synthesizing is performed by averaging the plurality of frames with the frames weighted according to the obtained frame displacement information.

27. The optical tomographic image generating apparatus according to claim 25, wherein the synthesizing is performed by averaging a result of one of parallel and rotational displacement of complex number data corresponding to each of the plurality of frames, based on the frame displacement information.

28. The optical tomographic image generating apparatus according to claim 25, further comprising:
a unit that obtains each one of the plurality of frames by synthesizing intensity signals acquired within a scanning time necessary for scanning the object in a predetermined direction perpendicular to an optical axis of the object, wherein synthesizing intensity signals is performed before synthesizing of the plurality of frames in complex number form.

29. The optical tomographic image generating apparatus according to claim 25, further comprising a unit that adjusts positions of the plurality of frames based on the frame displacement information, wherein the unit that synthesizes the plurality of frames synthesizes the plurality of frames by averaging the respective complex number data of each of the plurality of frames after the unit that adjusts positions adjusts the positions based on the frame displacement information, which is obtained by using a mean square.

30. The optical tomographic image generating apparatus according to claim 25, further comprising a unit that adjusts positions of the plurality of frames.

31. The optical tomographic image generating apparatus according to claim 25, wherein the unit for synthesizing synthesizes complex number form data of each of the plurality of frames by averaging, after the frames are subjected to one of parallel displacement and rotational displacement based on the frame displacement information.

32. The optical tomographic image generating apparatus according to claim 25, further comprising a unit that takes out a frame, wherein the unit that synthesizes averages the respective complex number data from each of a plurality of frames which are not taken out.

33. The optical tomographic image generating apparatus according to claim 32, further comprising a unit that determines whether or not a measurement error has occurred in a frame, wherein the unit that takes out a frame takes out a frame which is determined to have the measurement error.

34. The optical tomographic image generating apparatus according to claim 33, wherein the unit that determines whether or not a measurement error has occurred determines strain or falling-out of data caused by closing an eye in the frame as the measurement error.

35. The optical tomographic image generating apparatus according to claim 25, wherein the unit that synthesizes averages the respective complex number data based on information of one of parallel displacement and rotational displacement.

36. The optical tomographic image generating apparatus according to claim 35, wherein the object is an eye, and wherein the displacement is a result of an eye movement.

37. The optical tomographic image generating apparatus according to claim 25, wherein the unit that synthesizes subjects the respective complex number data to averaging after the unit that obtains the frame displacement information obtains the frame displacement information using a mean square.

38. The optical tomographic image generating apparatus according to claim 25, wherein the object is an eye, wherein the plurality of frames are obtained in a direction intersecting an optical axis of the eye, and wherein a positional difference between the frames is no more than several times of a traverse resolution.

39. The optical tomographic image generating apparatus according to claim 25, further comprising a unit that displays the generated tomographic image.

40. The optical tomographic image generating apparatus according to claim 25, further comprising a unit that converts the averaged complex number data into real number data, wherein the unit that generates the tomographic image generates the tomographic image based on the real number data.

\* \* \* \* \*